US010617376B2

(12) United States Patent
Liu et al.

(10) Patent No.: US 10,617,376 B2
(45) Date of Patent: Apr. 14, 2020

(54) C-ARM X-RAY IMAGING APPARATUS AND BASE FOR THE APPARATUS

(71) Applicant: GENERAL ELECTRIC COMPANY, Schenectady, NY (US)

(72) Inventors: Hailiang Liu, Beijing (CN); Jia Chen, Beijing (CN); Herve Kamdoum Choumin, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 179 days.

(21) Appl. No.: 15/860,967

(22) Filed: Jan. 3, 2018

(65) Prior Publication Data
US 2018/0184995 A1   Jul. 5, 2018

(30) Foreign Application Priority Data
Jan. 3, 2017   (CN) .......................... 2017 1 0000900

(51) Int. Cl.
*A61B 6/00*   (2006.01)
*H05G 1/02*   (2006.01)
*A61B 6/10*   (2006.01)

(52) U.S. Cl.
CPC ............ *A61B 6/4441* (2013.01); *A61B 6/102* (2013.01); *A61B 6/52* (2013.01); *H05G 1/02* (2013.01)

(58) Field of Classification Search
CPC ........... A61B 6/00; A61B 6/10; A61B 6/4441; A61B 6/52; A61B 6/102; A61B 6/44; A61B 6/4435; H05G 1/00; H05G 1/02
USPC ........ 378/193, 195, 196, 197, 204, 208, 210
See application file for complete search history.

(56) References Cited

U.S. PATENT DOCUMENTS 2,246,683 A  *  6/1941  Holt ...................... A47L 11/162
                                                      15/49.1

* cited by examiner

*Primary Examiner* — Jurie Yun
(74) *Attorney, Agent, or Firm* — Fletcher Yoder, P.C.

(57) ABSTRACT

Provided are a C-arm X-ray imaging apparatus and a base for the apparatus, the base comprising a drive member, a horizontal portion and a sunk portion. The sunk portion comprises a rotary disc connected to the horizontal portion and the drive member, and an upper surface of the rotary disc is flush with or lower than a lower surface of the horizontal portion. The rotary disc is configured to be rotatable about its center of rotation under the driving of the drive member so as to drive the base to rotate.

17 Claims, 5 Drawing Sheets

C-ARM X-RAY IMAGING APPARATUS AND BASE FOR THE APPARATUS

TECHNICAL FIELD

The present disclosure relates to the field of medical imaging, and more particularly to a C-arm X-ray imaging apparatus and a base for the apparatus.

BACKGROUND

C-arm X-ray imaging apparatuses can be used in various surgical operations for the imaging of a patient, wherein the C-arm generally has a C-shaped bracket, and two ends of the C-shaped bracket are used to arrange a bulb tube and a detector, respectively. The C-arm may be provided in an operating room by means of the base; in particular, the base may be L-shaped, the lower end of the L-shaped base may be supported on the floor, and the upper end may be used to connect to the C-arm. When in use, a bed carrying the patient can be moved to a pre-set position so that the patient lies between the bulb tube and the detector. With the continuous improvement of the C-arm, the C-shaped bracket can rotate around an ISO imaging center, with the point where the C-shaped bracket is connected to the L-shaped base as the pivot, so as to facilitate the imaging from different angles.

During surgery, some doctors are used to adjusting the patient bed to a lower position to adapt to his/her gesture. But when the bed surface is low, on one hand, the patient is too close to the bulb tube such that the patient is subject to a larger dose of X-ray radiation, and on the other hand, the bulb tube is likely to collide with the patient bed during the rotation of the C-shaped bracket, affecting the rotation angle of the C-shaped bracket.

Therefore, there is a need to provide a new C-arm X-ray imaging apparatus and a base for the apparatus, which can maintain an appropriate distance from the patient to the bulb tube when the patient bed surface is low, and prevent the bulb tube from colliding with the patient bed during the rotation of the C-shaped bracket.

SUMMARY

The embodiments described herein provide a new C-arm X-ray imaging apparatus and a base for the apparatus, which can maintain an appropriate distance from the patient to the bulb tube when the patient bed surface is low, and prevent the bulb tube from colliding with the patient bed during the rotation of the C-shaped bracket.

An exemplary non-limiting embodiment provides a base for a C-arm X-ray imaging apparatus, comprising a drive member, a horizontal portion and a sunk portion. The sunk portion comprises a rotary disc connected to the horizontal portion and the drive member, an upper surface of the rotary disc is flush with or lower than a lower surface of the horizontal portion, the rotary disc has a center of rotation, and the rotary disc is configured to be rotatable about its center of rotation under the driving of the drive member so as to drive the base to rotate.

An exemplary non-limiting embodiment provides a C-arm X-ray imaging apparatus, comprising the aforementioned base, and further comprising an accommodation cavity for accommodating the aforementioned sunk portion and drive member, the accommodation cavity being formed by providing an opening downward from an upper surface of a support table for supporting the C-arm X-ray imaging apparatus.

Other features and aspects will become apparent from the following detailed description, the drawings and the claims.

BRIEF DESCRIPTION OF THE DRAWINGS

The embodiments of the present disclosure described herein will be better understood with reference to the accompanying drawings in which.

DETAILED DESCRIPTION

Figure 1:
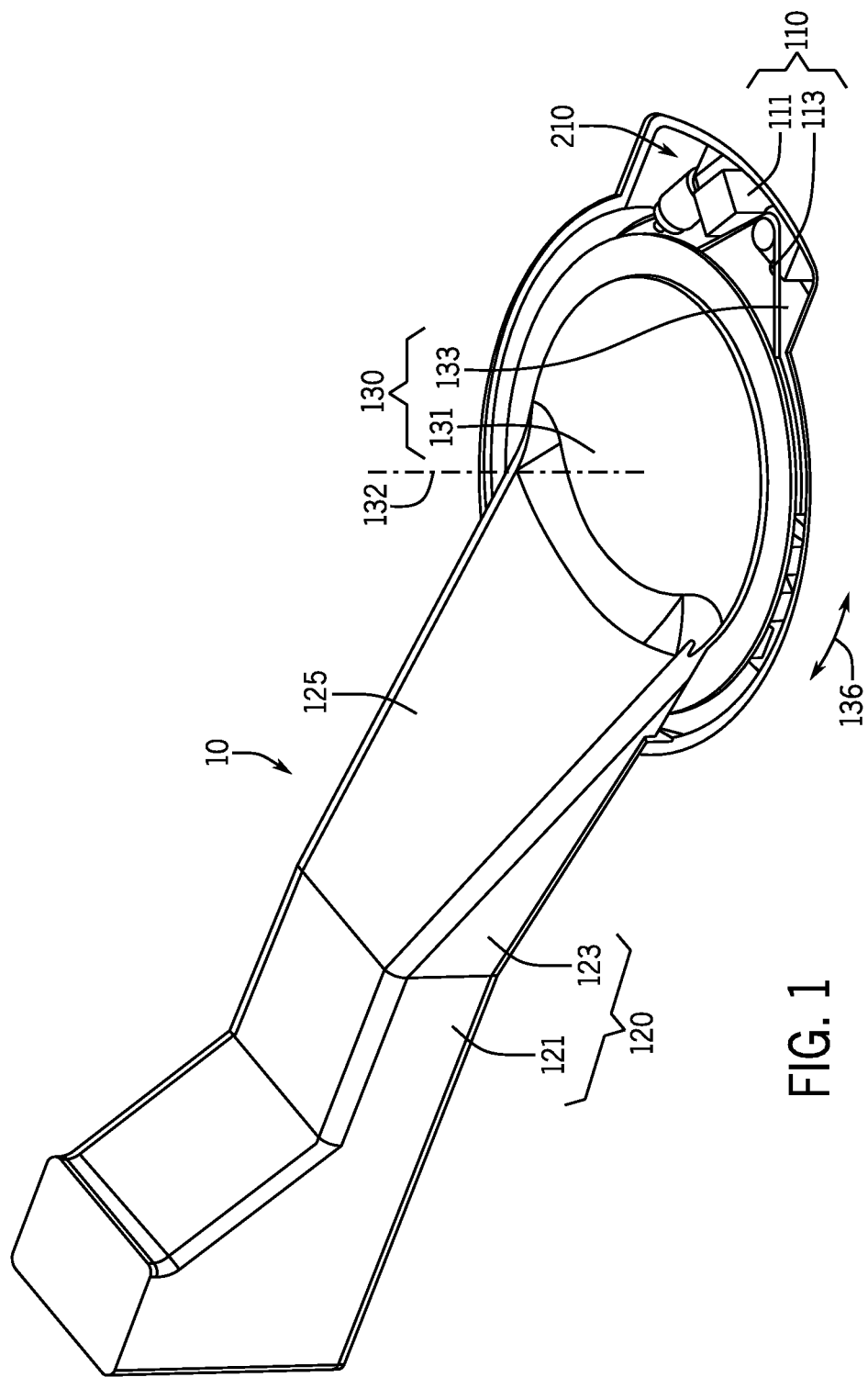
FIGS. 1, 2, 3 and 4 are all structural schematic views of a base according to at least one non-limiting embodiment of the present disclosure.
Figure 2:
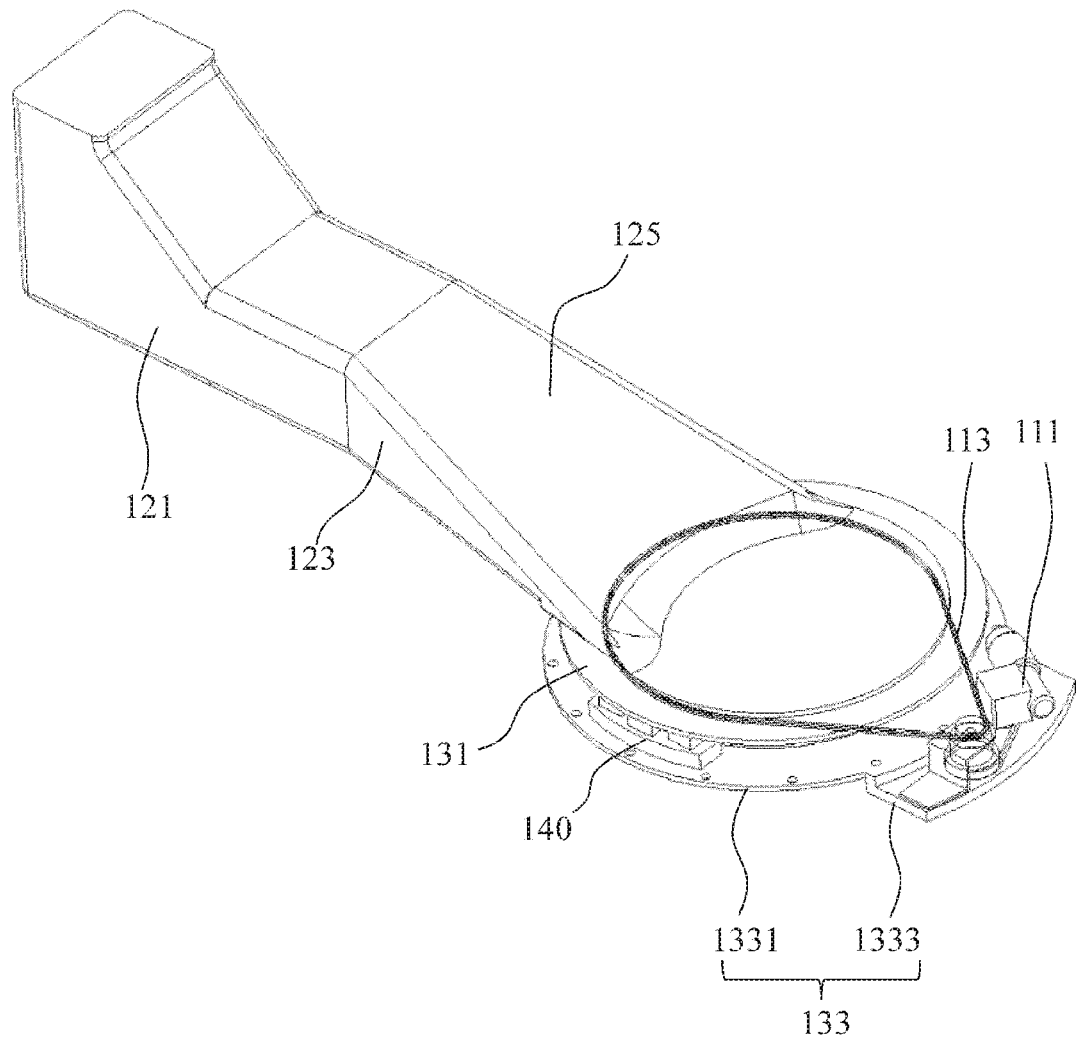
Figure 3:
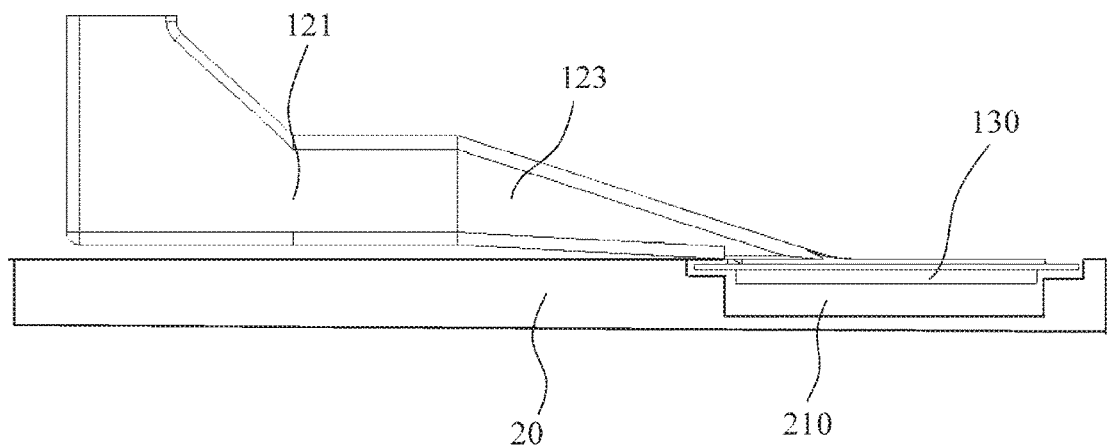

Specific embodiments of the present disclosure will be described below, and it will be noted that in the detailed description of these embodiments, for the sake of brevity and simplicity, it is not possible to describe all the features of the actual embodiments exhaustively. It should be appreciated that in the actual implementation of any of the embodiments, such as in the case of any engineering project or design project, in order to achieve the specific objectives of the developer and to meet system-related or business-related constraints, various specific decisions are often made, and this may change from one embodiment to another. In addition, it will also be appreciated that although efforts made during such a development may be complex and lengthy, for those of ordinary skill in the art pertinent to the present disclosure, some changes in the design, manufacture, or production etc. that are made on the basis of the technical contents disclosed in this disclosure are merely conventional techniques and it should not be construed as the present disclosure being insufficient.

Unless defined otherwise, all technical or scientific terms used in the claims and the description should be interpreted in the ordinary sense as understood by those of ordinary skill in the art to which this disclosure pertains. The terms "first", "second" and the like, as used in the description and claims of the present patent application, do not indicate any order, amount or importance, but are merely used to distinguish different constituent parts. The terms "a" or "an" and the like are not meant to be numerical limitation, but rather denote the presence of at least one. The terms "comprise" or "include" and the like are intended to mean that an element or thing appearing before the term "comprise" or "include" encompasses the element(s) or object(s) and equivalents thereof appearing after the term "comprise" or "include", and do not exclude other elements or objects. The terms "connect" or "connected" and the like are neither limited to physical or mechanical connections, nor limited to direct or indirect connections.

FIGS. 1, 2, 3 and 4 are all structural schematic views of a base provided according to at least one exemplary non-limiting embodiment of the present disclosure. A base 10 and an accommodation cavity 210 for accommodating a sunk portion 130 of the base 10 are shown in both FIGS. 1 and 3; the base 10 and a support table 20 for supporting the base 10 are shown in both FIGS. 3 and 4; and FIG. 4 also shows the base 10 and a cover body 230 for shielding the accommodation cavity 210. The base 20 is used in a C-arm X-ray imaging apparatus to support a bulb tube and detector at two ends of a C-shaped bracket.

As shown in FIGS. 1-4, the base 10 includes a drive member 110, a horizontal portion 120, and a sunk portion 130. The sunk portion 130 includes a rotary disc 131 connected to the horizontal portion 120 and the drive member 110. An upper surface of the rotary disc 131 is flush with or lower than a lower surface of the horizontal portion 120.

For example, the horizontal portion 120 may be generally L-shaped, one end of which may include a vertically upwardly extending portion for supporting the C-shaped bracket, the other end of the horizontal portion is connected to the rotary disc 131, and the rotary disc 131 is located below the horizontal portion 120 in the vertical direction. When the X-ray imaging apparatus is installed, the horizontal portion 120 may be arranged to be exposed on a table surface of the support table 20 of the apparatus, and the sunk portion 130 may be hidden below the table surface of the support table 20, for example, an accommodation space 210 for accommodating the sunk portion 130 may be provided in the support table 20. When the C-shaped bracket is in an upright position, the bulb tube on the bracket is opposite to the sunk portion 130 below the table surface. Therefore, the C-shaped bracket can be in a lower position without affecting its rotation as compared to placing the base as a whole on the table surface, i.e., when the C-shaped bracket is rotated in the lower position, the bulb tube can be prevented from colliding with patient bed above.

The rotary disc 131 has a center of rotation 132, and the rotary disc 131 may be configured to be rotatable about its center of rotation 132 (e.g., as indicated by arrow 136) under the driving of the drive member 110 so as to drive the base 10 to rotate as indicated in FIG. 1. Specifically, when the rotary disc 131 is rotated under the driving of the drive member 110, the horizontal portion 120 connected to the rotary disc 131 can also be rotated so that the C-shaped bracket and the bulb tube and the detector on the bracket can be in the required positions. The center of rotation 132 of the rotary disc 131 may be the geometric center of the rotary disc 131.

Optionally, the drive member 110 may comprise a motor 111 and a drive chain 113 connected to the motor 111, the drive chain 113 being used to engage with the rotary disc 131 to drive the rotary disc 131 to rotate under the driving of the motor 111.

Optionally, the horizontal portion 120 comprises a first connecting portion 121 for supporting the C-shaped bracket, and may also comprise a second connecting portion 123 connected between the first connecting portion 121 and the rotary disc 131. The distance between an upper surface and a lower surface of the second connecting portion 123 decreases gradually from the first connection portion 121 to the rotary disc 131, for example, the cross-section of the second connecting portion 123 may be substantially triangular, and with this design, the horizontal portion 120 can be more smoothly connected to the sunk portion 130 so as to avoid the occurrence of unnecessary corners at the connection of the two portions, which may damage the bulb tube on the C-shaped bracket.

In addition, the second connecting portion 123 is provided with an arc-shaped recess 125 in its upper surface; since the part of the second connecting portion connected to the rotary disc 131 has a certain height, the arc-shaped recess 125 is provided along the upper surface of the second connecting portion 123, so that it is possible for the position of the C-shaped bracket to be lower so as to be able to maintain a sufficient distance from the patient bed to avoid collision between the rotating C-shaped bracket and the patient bed.

Figure 4:
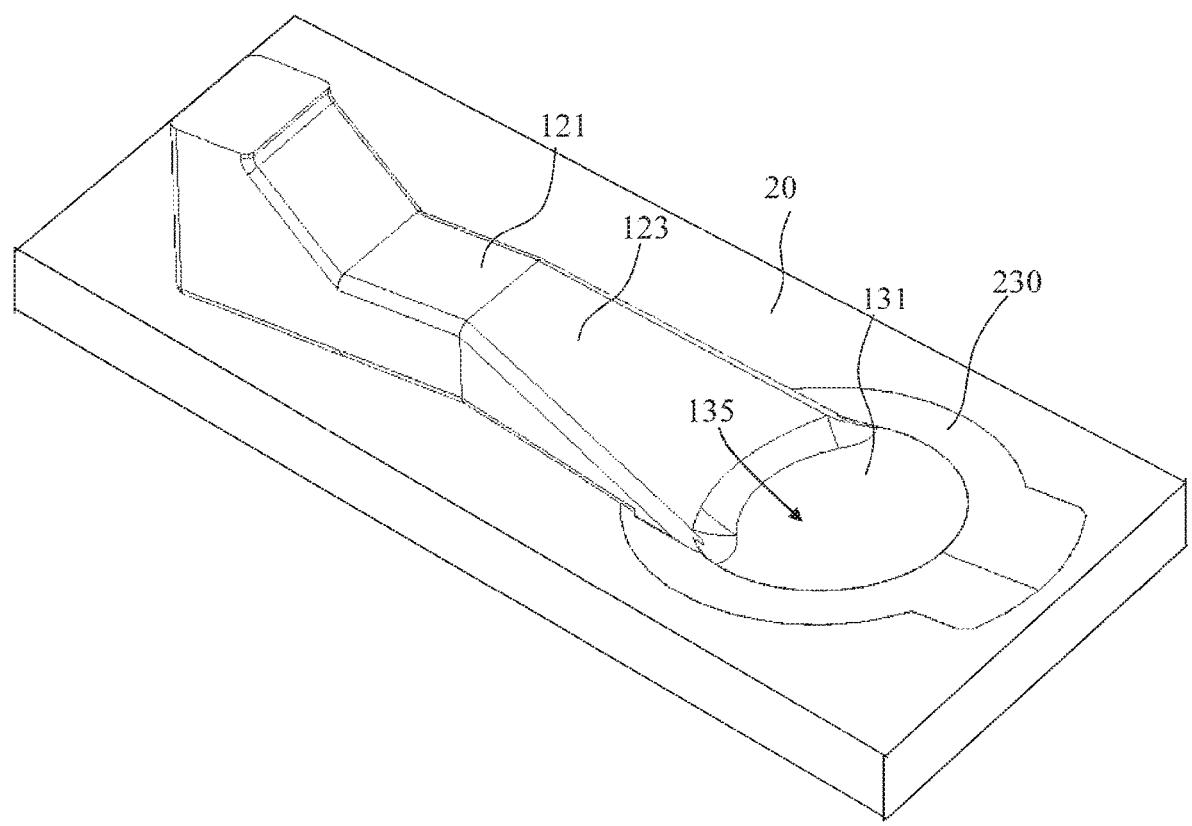

As shown in FIG. 4, in one embodiment, the upper surface of the rotary disc 131 may also be provided with an arc-shaped recess 135 to allow the C-shaped bracket to be positioned lower.

Optionally, the distance between the lower surface of the second connecting portion 123 and the lower surface of the first connecting portion 121 increases gradually from the first connecting portion 121 to the rotary disc 131, for example, the lower surface of the second connecting portion 123 is configured to have a certain slope or gradient so that the horizontal portion 120 can be more smoothly connected to the sunk portion 130 which has a relatively low position, and the reliability of the mechanical structure can be improved.

Optionally, the sunk portion 130 also includes a fixed chassis 133, and the fixed chassis 133 is provided below the rotary disc 131 to support the rotary disc 131.

In the base of a conventional C-arm X-ray imaging apparatus, the lower surface of the base is substantially in the same plane and is provided integrally on the table surface of the support table, and the drive motor is provided at the distal end of the L-shaped base and achieves the rotation of the base by driving the rotary disc at the other end of the L-shaped base by means of a complicated transmission relationship between a drive belt, a transmission shaft and a chain. In at least one embodiment, the motor 111 may be provided on the fixed chassis 133; in this way the motor 111 is disposed near the rotary disc 131, avoiding the use of a more complicated driving structure, saving costs, and enhancing the reliability of rotary driving. Since the motor 111 may be provided on the fixed chassis 133, the drive member 110 may be hidden with a sinker 130 below the table surface of the support table.

The fixed chassis 133 may also be provided with a brake device 140, which brake device 140 may be configured to be able to come into contact with the rotary disc for braking. For example, when the base 10 is rotated under the driving of the rotary disc 131, the brake device 140 may be controlled by an external controller to cause friction with the rotary disc so as to stop the base 10 from rotating.

Specifically, the fixed chassis 133 comprises a support portion 1331 and a protrusion 1333 protruding horizontally from the support portion 1331, the support portion 1331 is used to support the rotary disc 131, the protrusion 1333 may be used to arrange the motor 111, and the brake device 140 may be provided on the support portion 1331.

Optionally, the protrusion 1333 may be configured to be detachably connected to the support portion 1331 to facilitate servicing of the apparatus.

Figure 5:
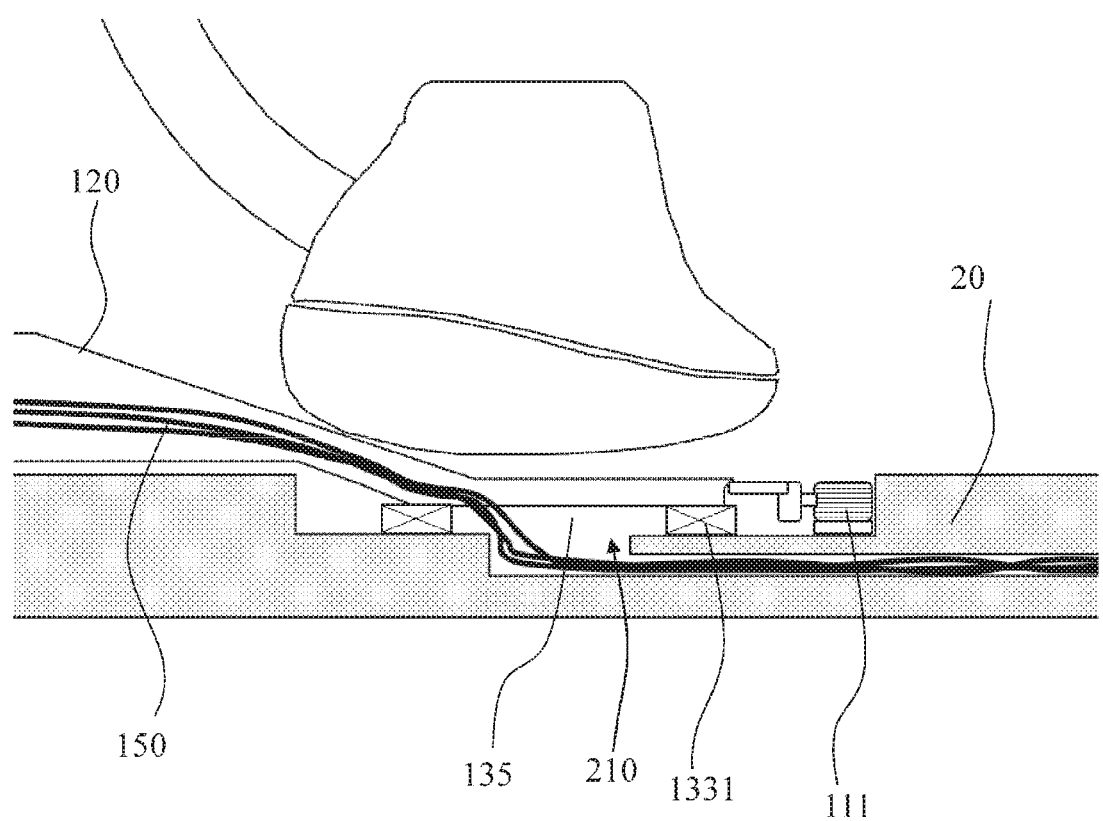
FIG. 5 schematically shows the structure of a wiring hole in a fixed chassis in FIG. 1 or 2.

FIG. 5 schematically shows the structure of a wiring hole in the fixed chassis 133. As shown in FIG. 5, the support portion 1331 of the fixed chassis 133 may be provided with a wiring hole 135, which penetrates through upper and lower surfaces of the support portion; for example, a hole may be formed in the middle of the support portion 1331 as the wiring hole 135, such that an electrical wire 150 drawn from the C-shaped bracket, the horizontal portion 120 or the sunk portion 130 of the base 10 can pass through the wiring hole so as to facilitate wiring; for example, the electrical wire 150 extends out of the base 10 below the table surface of the support table.

Figure 6:
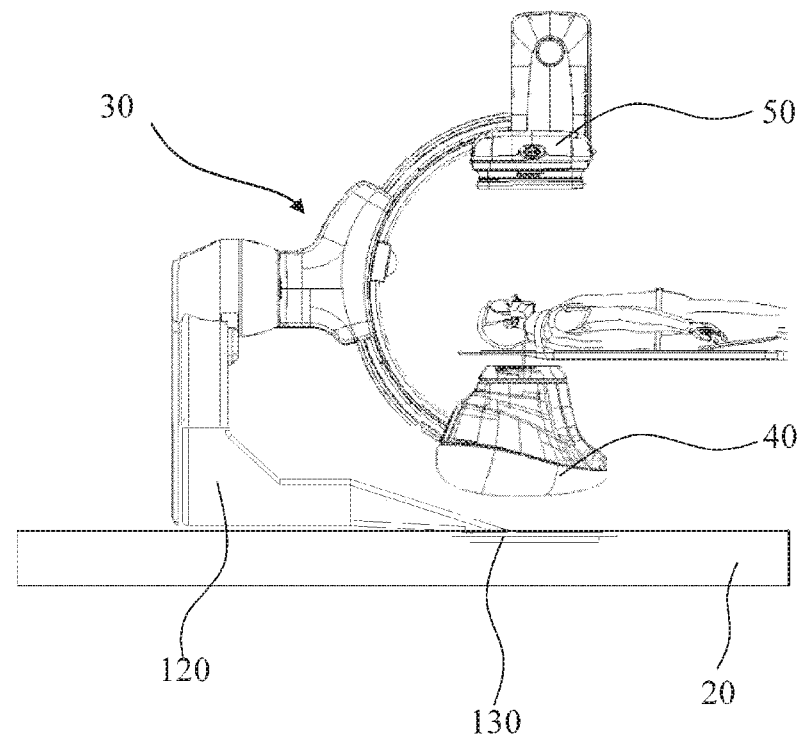
FIGS. 6 and 7 are both structural schematic views of a C-arm X-ray imaging apparatus according to at least one non-limiting embodiment of the present disclosure.
Figure 7:
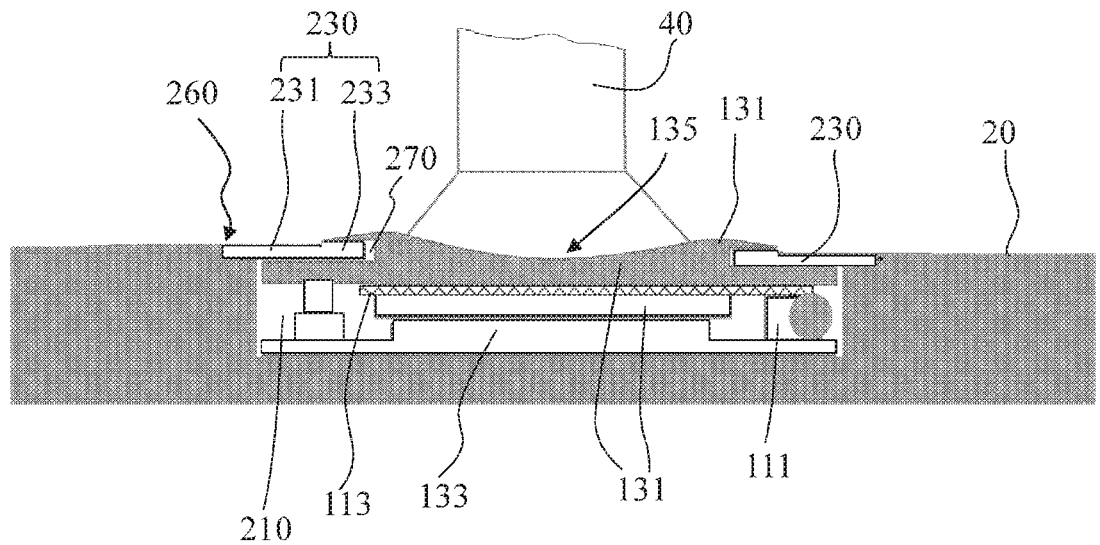

FIGS. 6 and 7 show a C-arm X-ray imaging apparatus provided according to at least one exemplary embodiment of the present disclosure. As shown in FIGS. 6 and 7, the C-arm X-ray imaging apparatus may comprise the base 10 in the aforementioned embodiment, and further comprises an accommodation cavity 210 for accommodating the sunk portion 130 and the drive member 110, wherein the accommodation cavity 210 may be formed by providing an opening downward from the upper surface of the support table 20, and the support table 20 is used to support the C-arm X-ray imaging apparatus. It will be appreciated by those skilled in the art that the support table 20 may be a floor or a variety of table-like support bodies provided on the floor, to enable the C-arm X-ray imaging apparatus, the patient bed and even a physician operating the apparatus to stand on the support table, and the table surface of the support table 20 is generally parallel with the horizontal plane.

Optionally, in order to protect the sunk portion 130 and the drive member 110 in the accommodation cavity 210, the C-arm X-ray imaging apparatus of the present embodiment may further comprise a cover body 230 which is provided on the support table 20 and used to shield the accommodation cavity 210. As shown in FIG. 7, the cover body 230 may be provided between the rotary disc 131 and the support table 20, i.e., the cover body 230 may be provided between the rotary disc 131 and a side wall of the accommodation cavity 210 to shield the part in the accommodation cavity 210 that is not shielded by the rotary disc 131. In a normal operation state of the C-arm X-ray imaging apparatus, the cover body 230 and the table surface of the support table 20 as well as the rotary disc 131 may be substantially in the same plane, and in an inspection or maintenance state, the cover body 230 can be lifted to expose the sunk portion 130 and the drive member 110 in the accommodation cavity 210.

Specifically, an opening 260 may be provided in the support table 20 along the side wall of the accommodation cavity 210, and an opening 270 may be provided in the rotary disc 231 along a side of the rotary disc 231; one end 231 of the cover body 230 may be provided in the opening 260, and the other end may be provided in the opening 270.

Optionally, the other end of the cover body 230 may have a bump 233, which bump 233 may be higher than the upper surface of the support table 20. As shown in FIG. 4, the cross-section of the cover body 230 is approximately "⌐"-shaped so that its horizontal end is provided in the opening 260 and the upwardly raised portion is higher than the table surface of the support table 20 and is embedded into the rotary disc 231 from the side of the rotary disc 231. In this way, it is not only possible to prevent the body fluid of the patient or a medicinal fluid from flowing into the accommodation cavity 210 along a gap and causing damage to the components in the accommodation cavity, but also possible to prevent the body fluid or the medicinal fluid from flowing into the rotary disc 231.

Furthermore, a seal (not shown in the figure) may be provided between the cover body 230 and the support table 20 to further prevent the body fluid of the patient or the medicinal fluid from flowing into the accommodation cavity 210. For example, the seal may be provided either between the side wall of the cover body 230 and the side wall of the accommodation cavity 210, or between the lower surface of the cover body 230 and the bottom wall of the opening 260.

It should be appreciated by those skilled in the art that the C-arm X-ray imaging apparatus may also comprise a C-shaped bracket 30, which C-shaped bracket 30 may be provided at one end of the horizontal portion 120 of the base 10, and a bulb tube 40 and a detector 50 are respectively provided at two ends of the C-shaped bracket 30, wherein the bulb tube 40 and the detector 50 are opposed to each other in the vertical direction. The C-shaped bracket 30 may be provided with a pivot at the location where the bracket is connected to the base 10, and rotate in a direction with the pivot as the center of rotation. When the C-shaped bracket is rotated to the upright position, the bulb tube 40 is opposite to the sunk portion 130. When the patient bed is moved between the bulb tube 40 and the detector 50, X-rays emitted from the bulb tube 40 pass through the patient and are detected by the detector 50, and the X-rays detected by the detector 50 are processed so as to be converted into an image signal, which enables the imaging of the patient.

In at least one embodiment, the upper surface of the rotary disc 131 of the sunk portion 130 is flush with or lower than the lower surface of the horizontal portion 120 so that the sunk portion 130 of the base 10 can be provided below the table surface of the support table 20, and therefore, the C-shaped bracket 30 can also be provided in a lower position; and when the physician adjusts the patient bed to a lower position to accommodate his or her own gesture, it is possible to prevent the patient from being irradiated with a large dose of X-rays when he or she is too close to the bulb tube; although the distance between the patient bed and the support table 20 is relatively small, the C-shaped bracket 30 does not collide with the patient bed during rotation because there is a sufficient distance between the bulb tube and the patient bed; and the drive member 110 drives the rotary disc 131 to rotate while rotating the horizontal portion 120 of the base 10.

Some exemplary embodiments have been described above. It should be appreciated, however, that various modifications may be made. For example, if the described techniques are performed in a different order and/or if the components in the described systems, architectures, apparatuses or circuits are combined in different ways and/or replaced or supplemented by additional components or their equivalents, an appropriate result can be achieved. Accordingly, other embodiments also fall within the scope of protection of the claims.

What is claimed is:

1. A base for a C-arm X-ray imaging apparatus, comprising:
   a drive member;
   a horizontal portion; and
   a sunk portion, wherein the sunk portion comprises a rotary disc connected to the horizontal portion and the drive member, an upper surface of the rotary disc is flush with or lower than a lower surface of the horizontal portion, the rotary disc has a center of rotation, and the rotary disc is configured to be rotatable about the center of rotation under the driving of the drive member so as to drive the base to rotate;
   wherein the horizontal portion comprises a first connecting portion for supporting a C-shaped bracket and a second connecting portion connected between the first connecting portion and the sunk portion of the rotary disc, and a distance between an upper surface and a lower surface of the second connecting portion decreases gradually from the first connecting portion to the rotary disc.

2. The base according to claim 1, wherein the second connecting portion comprises an arc-shaped recess in the upper surface of the second connecting portion.

3. The base according to claim 1, wherein a distance between the lower surface of the second connecting portion and a lower surface of the first connecting portion increases gradually from the first connecting portion to the rotary disc.

4. The base according to claim 1, wherein the drive member comprises a motor and a drive chain connected to the motor, the drive chain is engaged with the rotary disc, and the motor is used to drive the drive chain to rotate the rotary disc.

5. The base according to claim 4, wherein the sunk portion further comprises a fixed chassis which is disposed below the rotary disc and used to support the rotary disc.

6. The base according to claim 5, wherein the motor is disposed on the fixed chassis.

7. The base according to claim 6, wherein the fixed chassis comprises a support portion for supporting the rotary disc and a protrusion extending horizontally from the support portion, and the motor is disposed on the protrusion.

8. The base according to claim 7, wherein the protrusion is configured to be detachably connected to the support portion.

9. The base according to claim 7, wherein the support portion comprises a wiring hole which penetrates through upper and lower surfaces of the support portion.

10. The base according to claim 5, wherein the fixed chassis further comprises a brake device, which is configured to be able to come into contact with the rotary disc for braking.

11. A C-arm X-ray imaging apparatus, comprising:
a base according to claim 1, and
an accommodation cavity for accommodating the sunk portion and the drive member, the accommodation cavity being formed by providing an opening downward from an upper surface of a support table for supporting the C-arm X-ray imaging apparatus.

12. The C-arm X-ray imaging apparatus according to claim 11, wherein a cover body for shielding the accommodation cavity is provided on the support table.

13. The C-arm X-ray imaging apparatus according to claim 12, wherein the cover body is provided between the support table and the rotary disc, a first opening is provided in the support table along a side wall of the accommodation cavity, a second opening is provided in the rotary disc along a side of the rotary disc, one end of the cover body is disposed in the first opening, and the other end of the cover body is disposed in the second opening.

14. The C-arm X-ray imaging apparatus according to claim 13, wherein the other end of the cover body defines a bump, the bump being higher than an upper surface of the support table.

15. The C-arm X-ray imaging apparatus according to claim 12, further comprising a seal provided between the support table and the cover body.

16. A base for a C-arm X-ray imaging apparatus, comprising:
a drive member;
a horizontal portion; and
a sunk portion, wherein the sunk portion comprises a rotary disc connected to the horizontal portion and the drive member, an upper surface of the rotary disc is flush with or lower than a lower surface of the horizontal portion, the rotary disc has a center of rotation, and the rotary disc is configured to be rotatable about the center of rotation under the driving of the drive member so as to drive the base to rotate;
wherein the drive member comprises a motor and a drive chain connected to the motor, the drive chain is engaged with the rotary disc, and the motor is used to drive the drive chain to rotate the rotary disc, and
wherein the sunk portion further comprises a fixed chassis which is disposed below the rotary disc and used to support the rotary disc.

17. A C-arm X-ray imaging apparatus, comprising:
a base comprising:
a drive member;
a horizontal portion; and
a sunk portion, wherein the sunk portion comprises a rotary disc connected to the horizontal portion and the drive member, an upper surface of the rotary disc is flush with or lower than a lower surface of the horizontal portion, the rotary disc has a center of rotation, and the rotary disc is configured to be rotatable about the center of rotation under the driving of the drive member so as to drive the base to rotate; and
an accommodation cavity for accommodating the sunk portion and the drive member, the accommodation cavity being formed by providing an opening downward from an upper surface of a support table for supporting the C-arm X-ray imaging apparatus.

* * * * *